(12) United States Patent
Fahim et al.

(10) Patent No.: US 11,413,142 B2
(45) Date of Patent: Aug. 16, 2022

(54) STENT ASSEMBLY FOR USE IN PROSTHETIC HEART VALVES

(71) Applicant: St. Jude Medical, Cardiology Division, Inc., St. Paul, MN (US)

(72) Inventors: Mina S. Fahim, Shoreview, MN (US); Peter N. Braido, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 203 days.

(21) Appl. No.: 16/571,688

(22) Filed: Sep. 16, 2019

(65) Prior Publication Data

US 2020/0008939 A1 Jan. 9, 2020

Related U.S. Application Data

(63) Continuation of application No. 15/649,964, filed on Jul. 14, 2017, now Pat. No. 10,420,641, which is a
(Continued)

(51) Int. Cl.
*A61F 2/844* (2013.01)
*A61F 2/24* (2006.01)
*A61F 2/90* (2013.01)

(52) U.S. Cl.
CPC .......... *A61F 2/2418* (2013.01); *A61F 2/2412* (2013.01); *A61F 2/844* (2013.01);
(Continued)

(58) Field of Classification Search
CPC .... A61F 2/86; A61F 2/90; A61F 2/844; A61F 2/2412; A61F 2/2418; A61F 2250/0069
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 B4 11/2005
(Continued)

OTHER PUBLICATIONS

"Catheter-Implanted Prosthetic Heart Valves: Transluminal Catheter Implantation of a New Expandable Artificial Heart Valve in the Descending Thoracic Aorta in Isolated Vessels and Closed Chest Pigs", Knudsen et al., The International Journal of Artificial Organs, vol. 16, No. 5, May 1993, pp. 253-262.
(Continued)

*Primary Examiner* — Brian A Dukert
(74) *Attorney, Agent, or Firm* — Wei & Sleman LLP

(57) ABSTRACT

A prosthetic heart valve having a cuff attached to a stent provides a seal for preventing paravalvular leakage. The cuff may be constructed from known sealing materials to fill in and around paravalvular leakage gaps, while continuously collapsing down into a low profile volume within the stent. The cuff has a first cuff portion positioned on the luminal surface of the stent and a second cuff portion. The second cuff portion has a deployed configuration in which a region of the second cuff portion is spaced from the abluminal surface of the stent and an initial configuration different from the deployed configuration.

11 Claims, 9 Drawing Sheets

Related U.S. Application Data continuation of application No. 14/713,399, filed on May 15, 2015, now Pat. No. 9,757,230.

(60) Provisional application No. 61/994,187, filed on May 16, 2014.

(52) U.S. Cl.
CPC ........ *A61F 2/90* (2013.01); *A61F 2210/0014* (2013.01); *A61F 2230/0065* (2013.01); *A61F 2250/0069* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |

(56) References Cited

U.S. PATENT DOCUMENTS

| | | | |
|---|---|---|---|
| 8,685,080 B2 | 4/2014 | White | |
| 8,728,154 B2 | 5/2014 | Alkhatib | |
| 8,747,459 B2 | 6/2014 | Nguyen et al. | |
| 8,764,820 B2 | 7/2014 | Dehdashtian et al. | |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,834,563 B2 | 9/2014 | Righini | |
| 8,840,661 B2 | 9/2014 | Manasse | |
| 8,840,663 B2 | 9/2014 | Salahieh et al. | |
| 8,876,894 B2 | 11/2014 | Tuval et al. | |
| 8,876,895 B2 | 11/2014 | Tuval et al. | |
| 8,940,040 B2 | 1/2015 | Shahriari | |
| 8,945,209 B2 | 2/2015 | Bonyuet et al. | |
| 8,961,595 B2 | 2/2015 | Alkhatib | |
| 8,974,523 B2 | 3/2015 | Thill et al. | |
| 8,974,524 B2 | 3/2015 | Yeung et al. | |
| 10,195,025 B2 * | 2/2019 | Levi | A61F 2/2427 |
| 2002/0036220 A1 | 3/2002 | Gabbay | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0111111 A1 | 6/2004 | Lin | |
| 2004/0210304 A1 | 10/2004 | Seguin et al. | |
| 2004/0260389 A1 | 12/2004 | Case et al. | |
| 2005/0096726 A1 | 5/2005 | Sequin et al. | |
| 2005/0137682 A1 | 6/2005 | Justino | |
| 2005/0137695 A1 | 6/2005 | Salahieh et al. | |
| 2005/0137697 A1 | 6/2005 | Salahieh et al. | |
| 2005/0203605 A1 | 9/2005 | Dolan | |
| 2005/0240200 A1 | 10/2005 | Bergheim | |
| 2005/0256566 A1 | 11/2005 | Gabbay | |
| 2006/0008497 A1 | 1/2006 | Gabbay | |
| 2006/0058872 A1 | 3/2006 | Salahieh et al. | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0161249 A1 | 7/2006 | Realyvasquez et al. | |
| 2006/0173532 A1 | 8/2006 | Flagle et al. | |
| 2006/0178740 A1 | 8/2006 | Stacchino et al. | |
| 2006/0195180 A1 | 8/2006 | Kheradvar et al. | |
| 2006/0206202 A1 | 9/2006 | Bonhoeffer et al. | |
| 2006/0241744 A1 | 10/2006 | Beith | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0276874 A1 | 12/2006 | Wilson et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0198097 A1 | 8/2007 | Zegdi | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0099653 A1 | 4/2009 | Suri et al. | |
| 2009/0112309 A1 | 4/2009 | Jaramillo et al. | |
| 2009/0138079 A1 | 5/2009 | Tuval et al. | |
| 2009/0276027 A1 | 11/2009 | Glynn | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0168844 A1 | 7/2010 | Toomes et al. | |
| 2010/0185277 A1 | 7/2010 | Braido et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0234940 A1 | 9/2010 | Dolan | |
| 2010/0249911 A1 | 9/2010 | Alkhatib | |
| 2010/0249923 A1 | 9/2010 | Alkhatib et al. | |
| 2010/0286768 A1 | 11/2010 | Alkhatib | |
| 2010/0298931 A1 | 11/2010 | Quadri et al. | |
| 2011/0029072 A1 | 2/2011 | Gabbay | |
| 2011/0054466 A1 | 3/2011 | Rothstein et al. | |
| 2011/0098800 A1 | 4/2011 | Braido et al. | |
| 2011/0098802 A1 | 4/2011 | Braido et al. | |
| 2011/0137397 A1 | 6/2011 | Chau et al. | |
| 2011/0172765 A1 | 7/2011 | Nguyen et al. | |
| 2011/0208283 A1 | 8/2011 | Rust | |
| 2011/0264206 A1 | 10/2011 | Tabor | |
| 2012/0035722 A1 | 2/2012 | Tuval | |
| 2012/0078347 A1 | 3/2012 | Braido et al. | |
| 2012/0101572 A1 | 4/2012 | Kovalsky et al. | |
| 2012/0123529 A1 | 5/2012 | Levi et al. | |
| 2012/0303116 A1 | 11/2012 | Gorman, III et al. | |
| 2013/0274873 A1 | 10/2013 | Delaloye et al. | |
| 2013/0331929 A1 | 12/2013 | Mitra et al. | |
| 2014/0121763 A1 | 5/2014 | Duffy et al. | |
| 2014/0155997 A1 | 6/2014 | Braido | |
| 2014/0214159 A1 | 7/2014 | Vidlund et al. | |
| 2014/0228946 A1 | 8/2014 | Chau et al. | |
| 2014/0277417 A1 * | 9/2014 | Schraut | A61F 2/2403 623/2.17 |
| 2014/0277419 A1 * | 9/2014 | Garde | A61F 2/2403 623/2.18 |
| 2014/0303719 A1 | 10/2014 | Cox et al. | |
| 2014/0324164 A1 | 10/2014 | Gross et al. | |
| 2014/0343671 A1 | 11/2014 | Yohanan et al. | |
| 2014/0350668 A1 | 11/2014 | Delaloye et al. | |
| 2014/0350669 A1 | 11/2014 | Gillespie et al. | |

FOREIGN PATENT DOCUMENTS

| | | |
|---|---|---|
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1758523 B1 | 3/2007 |
| EP | 1926455 A2 | 6/2008 |
| EP | 2537487 A1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 2001049213 A2 | 7/2001 |
| WO | 0154625 A1 | 8/2001 |
| WO | 01056500 A2 | 8/2001 |
| WO | 0176510 A2 | 10/2001 |

(56) References Cited

FOREIGN PATENT DOCUMENTS

| WO | 2002036048 A1 | 5/2002 |
|---|---|---|
| WO | 0247575 A2 | 6/2002 |
| WO | 02067782 A2 | 9/2002 |
| WO | 03047468 A1 | 6/2003 |
| WO | 2005070343 A1 | 8/2005 |
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 2010008549 A1 | 1/2010 |
| WO | 2010096176 A1 | 8/2010 |
| WO | 2010098857 A1 | 9/2010 |
| WO | 2013/028387 A2 | 2/2013 |
| WO | 2013059743 A1 | 4/2013 |
| WO | 2014164149 A1 | 10/2014 |
| WO | 2015077274 A1 | 5/2015 |

OTHER PUBLICATIONS

"Closed Heart Surgery: Back to the Future", Samuel V. Lichtenstein, The Journal of Thoracic and Cardiovascular Surgery, vol. 131, No. 5, May 2006, pp. 941-943.
"Direct-Access Valve Replacement", Christoph H. Huber, et al., Journal of the American College of Cardiology, vol. 46, No. 2, (Jul. 19, 2005).
"Minimally invasive cardiac surgery", M. J. Mack, Surgical Endoscopy, 2006, 20:S488-S492, DOI: 10.1007/s00464-006-0110-8 (presented Mar. 23, 2006).
"Percutaneous Aortic Valve Implantation Retrograde From the Femoral Artery", John G. Webb et al., Circulation, 2006; 113:842-850 (Feb. 2, 2006).
"Percutaneous Aortic Valve Replacement: Resection Before Implantation", Quaden, Rene et al., European J. of Cardio-Thoracic Surgery, vol. 27, No. 5, May 2005, pp. 836-840.
"Transapical aortic valve implantation: an animal feasibility study"; Todd M. Dewey et al., The annals of thoracic surgery 2006; 82: 110-6 (Feb. 13, 2006).
"Transapical Approach for Sutureless Stent-Fixed Aortic Valve Implantation: Experimental Results", Th. Walther et al., European Journal of Cardio-Thoracic Surgery, vol. 29, No. 5, May 2006, pp. 703-708.
"Transapical Transcatheter Aortic Valve Implantation in Humans", Samuel V. Lichtenstein et al., Circulation. 2006; 114: 591-596 (Jul. 31, 2006).
"Transcatheter Umbrella Closure of Valvular and Paravalvular Leaks", Hourihan et al., Journal of the American College of Cardiology, vol. 20, No. 6, Nov. 1992, pp. 1371-1377.
"Transluminal Aortic Valve Placement. A Feasability Study with a Newly Designed Collapsible Aortic Valve", Moazami et al., ASAIO Journal, vol. 42, No. 5, 1996, pp. M381-M385.
"Transluminal Catheter Implanted Prosthetic Heart Valves", Andersen, H. R., International Journal of Angiology, vol. 7, No. 2, Mar. 1998, pp. 102-106.
"Transluminal Implantation of Artificial Heart Valves", Andersen, H. R., et al., European Heart Journal, vol. 13, No. 5, May 1992, pp. 704-708.
Braido, et al., U.S. Appl. No. 29/375,243, filed Sep. 20, 2010, titled "Surgical Stent Assembly".

Buellesfeld et al., "Treatment of Paravalvular Leaks Through Inverventional Techniques", Multimedia Manual of Cardithoracic Surgery, Department of Cardiology, Ben University Hospital, Jan. 2011.
De Cicco, et al., "Aortic Valve Periprosthetic Leakage: Anatomic Observations and Surgical Results", The Annals of Thoracic Surgery, vol. 79, No. 5, May 2005, pp. 1480-1485.
Gössl and Rihal, "Percutaneous Treatment of Aortic and Mitral Valve Paravalvular Regurgitation", Current Cardiology Reports, vol. 15, No. 8, Aug. 2013, pp. 1-8.
Heat Advisor, "Heart repairs without surgery. Minimally invasive procedures aim to correct valve leakage", Sep. 2004, PubMed ID 15586429.
Is it Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Muñoz, Daniel Rodriguez, Carla Lázaro Rivera, and Jose Luis Zamorano Gómez, "Guidance of Treatment of Perivalvular Prosthetic Leaks", Current Cardiology Reports, vol. 16, No. 1, Nov. 2013, pp. 1-6.
Rohde, I., Masch, J.-M., Theisen-Kunde, D., Marczynski-Bühlow, M., Bombien Quaden, R., Lutter, G. and Brinkmann, R., "Resection of Calcified Aortic Heart Leaflets in Vitro by Q-Switched 2?μm Microsecond Laser Radiation", Journal of Cardiac Surgery, vol. 30, No. 2, Feb. 2015, pp. 157-162. doi: 10.1111/jocs.12481.
Ruiz, Carlos, Overview of PRE-CE Mark Transcatheter Aortic Valve Technologies, Euro PCR, dated May 25, 2010.
Swiatkiewicz et al., "Percutaneous Closure of Mitral Perivalvular Leak", Kardiologia Polska, vol. 67, No. 7, 2009, pp. 762-764.
Transcatheter Valve Repair, Hijazi et al., CRC Press, Jan. 2006, pp. 165-186.
Buellesfeld, et al., "Treatment of paravalvular leaks through inverventional techniques," Multimed Man Cardiothorac Surg., Department of Cardiology, Ben University Hospital, pp. 1-8, Jan. 2011.
De Cicco, et al., "Aortic valve periprosthetic leakage: anatomic observations and surgical results," The Annals of thoracic surgery, vol. 79, No. 5, pp. 1480-1485, May 2005.
European Search Report for Application No. EP17177736, dated Nov. 22, 2017.
Gössl, et al., "Percutaneous treatment of aortic and mitral valve paravalvular regurgitation," Current Cardiology Reports, vol. 15, No. 8., pp. 1-8, Aug. 2013.
Heat Advisor, "Heart repairs without surgery, Minimally invasive procedures aim to correct valve leakage", Technology Frontier, Sep. 2004, PubMed ID 15586429.
Hourihan, et al., "Transcatheter Umbrella Closure of Valvular and Paravalvular Leaks," Journal of the American College of Cardiology, vol. 20, No. 6, pp. 1371-1377, Nov. 1992.
International Search Report and Written Opinion for Application No. PCT/US2015/030945 dated Jul. 31, 2015.
Muñoz, et al., "Guidance of treatment of perivalvular prosthetic leaks.", Current cardiology reports, 16.430, 6 pages, Jan. 2014.
Rohde,et al., "Resection of Calcified Aortic Heart Leaflets in Vitro by Q-Switched 2 μm Microsecond Laser Radiation", Journal of Cardiac Surgery, 30(2): 157-62. Feb. 2015.
Swiatkiewicz, et al., "Percutaneous closure of mitral perivalvular leak," Kardiologia Polska, vol. 67, No. 7, pp. 762-764, Jul. 2009.

\* cited by examiner

STENT ASSEMBLY FOR USE IN PROSTHETIC HEART VALVES

CROSS-REFERENCE TO RELATED APPLICATIONS

The present application is a continuation of U.S. patent application Ser. No. 15/649,964, filed Jul. 14, 2017, now U.S. Pat. No. 9,757,230, which is a continuation of U.S. patent application Ser. No. 14/713,399, filed May 15, 2015, which claims the benefit of the filing date of U.S. Provisional Patent Application No. 61/994,187, filed May 16, 2014, the disclosures of which are hereby incorporated herein by reference.

BACKGROUND OF THE DISCLOSURE

The present disclosure relates to a stent assembly for heart valve replacement and, in particular, to collapsible prosthetic heart valves. More particularly, the present disclosure relates to collapsible prosthetic transcatheter heart valves which minimize or reduce paravalvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve is first collapsed or crimped to reduce its circumferential size. It is therefore desirable that the valve have a low profile or volume to minimize the size of the delivery apparatus.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

There is a need for improvements to prosthetic heart valves, and specifically, to collapsible prosthetic heart valves that would reduce the likelihood of paravalvular leakage due to gaps between the implanted prosthetic heart valve and patient tissue.

BRIEF SUMMARY OF THE DISCLOSURE

In one embodiment of the present disclosure there is described a stent assembly for use in a prosthetic heart valve for replacing a native valve. The prosthetic heart valve includes a stent having a luminal surface and an abluminal surface extending between a distal end and a proximal end thereof. A valve may be disposed within the stent. A cuff may be coupled to the stent having a first orientation and a second orientation. A plurality of members may be provided having a distal end coupled to the stent and a proximal end coupled to the cuff. The plurality of members has a first state when the cuff is arranged in the first orientation and a second state when the cuff is arranged in the second orientation.

In another embodiment of the present disclosure there is also described a stent assembly for use in a prosthetic heart valve for replacing a native valve. The prosthetic heart valve includes a stent having a proximal end and an abluminal surface. A valve may be disposed within the stent. A cuff may be coupled to the stent by a plurality of members having a relaxed state and a tensioned state for orienting at least a portion of the cuff at least partially disposed on the abluminal surface when the plurality of members are in a relaxed state.

In a further embodiment of the present disclosure there is also described a stent assembly for use in a prosthetic heart valve for replacing a native valve. The prosthetic heart valve includes a stent. A valve may be disposed within the stent. A cuff may be coupled to the stent having a first orientation and a second orientation. A plurality of members may be coupled between the stent and cuff. The members are configured to arrange the cuff between the first and second orientations, wherein the members remain coupled to the stent and cuff after replacement of the native valve.

In a further embodiment of the present disclosure there is also described a stent assembly for use in a prosthetic heart valve for replacing a native valve. The prosthetic heart valve includes a stent configured to have a collapsed condition and an expanded condition. The stent has a luminal surface and an abluminal surface extending between a distal end and a proximal end thereof. A valve assembly may be disposed within the stent. The valve assembly may include a plurality of leaflets and a cuff having a portion at least partially disposed on the luminal surface of the stent. At least a portion of the cuff has a first orientation extending outwardly of the proximal end of the stent or at least partially disposed on the abluminal surface of the stent and a second orientation with a portion of the cuff at least partially disposed on the abluminal surface of the stent. A plurality of elongated elastic members has a distal end coupled to the stent and a proximal end coupled to the cuff at circumferentially spaced apart locations. The plurality of elastic members has a tensioned state when the cuff is arranged in the first orientation and a relaxed state when the cuff is arranged in the second orientation.

In a further embodiment of the present disclosure there is also described a stent assembly for use in a prosthetic heart valve for replacing a native valve. The prosthetic heart valve includes a stent. A cuff may be coupled to the stent having a first orientation and a second orientation. A plurality of inverting members may be coupled between the stent and cuff. The members are configured to arrange the cuff between the first and second orientations, wherein the inverting members remain coupled to the stent and cuff after replacement of the native valve.

BRIEF DESCRIPTION OF THE DRAWINGS

Various embodiments of the presently disclosed stent assembly and prosthetic heart valves may be more fully understood with reference to the following detailed description when read with the accompanying drawings, in which.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Like reference numbers refer to similar or identical elements throughout the disclosure.

Figure 1:
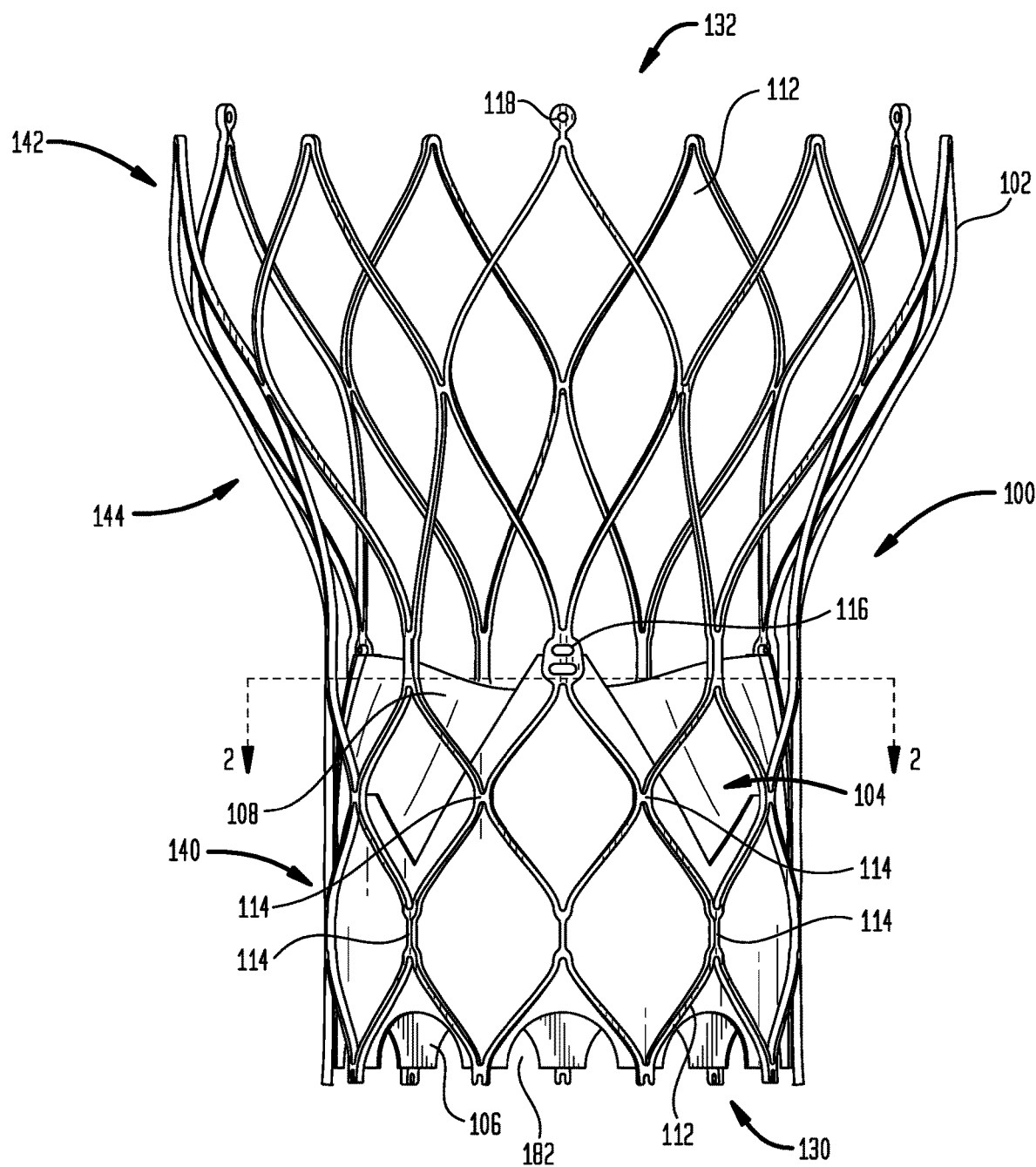
FIG. 1 is a front view of a conventional collapsible prosthetic heart valve.

FIG. 1 shows a collapsible stent-supported prosthetic heart valve 100 known in the art. The prosthetic heart valve 100 is designed to replace the function of a native tricuspid, bicuspid or unicuspid valve of a patient, such as a native aortic valve. It should be noted that while the embodiments herein are described predominately in connection with their use with a prosthetic aortic valve and a stent having a shape as illustrated in FIG. 1, the embodiments may also be used with tricuspid valves, pulmonic valves, and bicuspid valves, such as the mitral valve, and with stents having different shapes, such as those having a flared or conical annulus section, a less-bulbous aortic section, and the like, and a differently shaped transition section.

The prosthetic heart valve 100 includes a stent constructed as a frame 102 from a plurality of attached cells 112, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including shape memory alloys known as Nitinol. Suitable synthetic polymers for use as a stent include, but are not limited to, thermoplastics, such as polyolefins, polyesters, polyamides, polysulfones, acrylics, polyacrylonitriles, polyetheretherketone, and polyaramides.

The stent 102 extends from a proximal or annulus end 130 to a distal or aortic end 132, and includes an annulus section 104 adjacent the proximal end 130 and an aortic section 142 adjacent the distal end 132. The annulus section 104 has a relatively small cross-section in the expanded condition, while the aortic section 142 has a relatively large cross-section in the expanded condition. The annulus section 104 may be in the form of a cylinder having a substantially constant diameter along its length. A transition section 144 may taper outwardly from the annulus section 104 to the aortic section 142. Each of the sections of the stent 102 includes a plurality of cells 112 connected to one another in one or more annular rows around the stent 102. For example, as shown in FIG. 1, the annulus section 104 may have two annular rows of complete cells 112 and the aortic section 142 and the transition section 144 may each have one or more annular rows of complete or partial cells 112. The cells 112 in the aortic section 142 may be larger than the cells 112 in the annulus section 104. The larger cells 112 in the aortic section 142 better enable the prosthetic valve 100 to be positioned without the stent structure 102 interfering with blood flow to the coronary arteries. The cells 112 may be connected circumferentially to each other by runners 114 arranged about the stent 102.

The stent 102 may include one or more retaining elements 118 at the distal end 132 thereof, the retaining elements 118 being sized and shaped to cooperate with retaining structures provided on a deployment device (not shown). The engagement of the retaining elements 118 with the retaining structures on the deployment device helps maintain the prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The stent 102 may also include a plurality of commissure points 116 for mounting the commissures (not identified) where two leaflets 108 come together to the stent 102. As can be seen in FIG. 1, the commissure points 116 may lay at the intersection of four cells 112, two of the cells 112 being adjacent one another in the same annular row, and the other two cells 112 being in different annular rows and lying in end-to-end relationship. In one embodiment, the commissure points 116 are positioned entirely within the annulus section 104 or at the juncture of annulus section 104 and the transition section 144. The commissure points 116 may include one or more eyelets which facilitate the suturing of the leaflet commissure to the stent.

The prosthetic heart valve 100 includes a valve assembly 140 preferably positioned in the annulus section 104. The valve assembly 140 may be mounted to the stent 102 by suturing the commissures of the leaflets 108 to the commissure points 116 and suturing other portions of the valve assembly 140 to the stent 102, or by other methods known in the art. The valve assembly 140 may include a cuff 106 and a plurality of leaflets 108 which collectively function as a one-way valve by coapting with one another. FIG. 1 illustrates a prosthetic heart valve for replacing a native tricuspid valve, such as the aortic valve. Accordingly, the prosthetic heart valve 100 is shown in FIG. 1 with three leaflets 108, as well as three commissure points 116. However, it will be appreciated that the prosthetic heart valves according to aspects of the disclosure may have a greater or lesser number of leaflets 108 and commissure points 116. The valve assembly 140 may be wholly or partly formed of any suitable biological material or polymer. Examples of biological materials suitable for the valve assembly 140 include, but are not limited to, porcine or bovine pericardial tissue. Examples of polymers suitable for the valve assembly 140 include, but are not limited to, polyurethane, silicone, PTFE and polyester. In at least some examples, portions of valve assembly 140, the cuff and the suture used may include an ultra-high molecular weight polyethylene.

Although the cuff 106 is shown in FIG. 1 as being disposed on the luminal or inner surface of the annulus section 104, it is contemplated that the cuff 106 may be disposed on the abluminal or outer surface of annulus section 104, or may cover all or part of either or both of the luminal and abluminal surfaces of the annulus section 104. Both the cuff 106 and the leaflets 108 may be wholly or partly formed of any suitable biological material or polymer, including those, such as PTFE, described above in connection with the prosthetic heart valve 100. Additionally, the cuff 106 may be formed from polyurethane copolymers or include ultra-high molecular weight polyethylene.

As is shown in FIG. 1, in one example the entirety of the valve assembly 140, including the leaflet commissures, is positioned in the annulus section 104 of the stent 102. When opened, the leaflets may extend further into the transition region 144 or may be designed such that they remain substantially completely within the annulus region 104. In this embodiment, substantially the entirety of the valve assembly 140 is positioned between the proximal end 130 of stent 102 and the commissure points 116, and none of the valve assembly is positioned between the commissure points 116 and the distal end 132 of the stent 102.

In operation, the embodiments of the prosthetic heart valve 100 described above may be used to replace a native heart valve, such as the aortic valve, a surgical heart valve or a heart valve that has undergone a surgical procedure. The prosthetic heart valve 100 may be delivered to the desired site (e.g., near a native aortic annulus) using any suitable delivery device. During delivery, the prosthetic heart valve 100 is disposed inside the delivery device in the collapsed condition. The delivery device may be introduced into a patient using any known procedures, such as a transfemoral, transapical or transseptal approach. Once the delivery device has reached the target site, the user may deploy the prosthetic heart valve 100. Upon deployment, the prosthetic heart valve 100 expands into secure engagement within the native aortic annulus. When the prosthetic heart valve 100 is properly positioned inside the heart, it works as a one-way valve, allowing blood to flow in one direction and preventing blood from flowing in the opposite direction.

Figure 2:
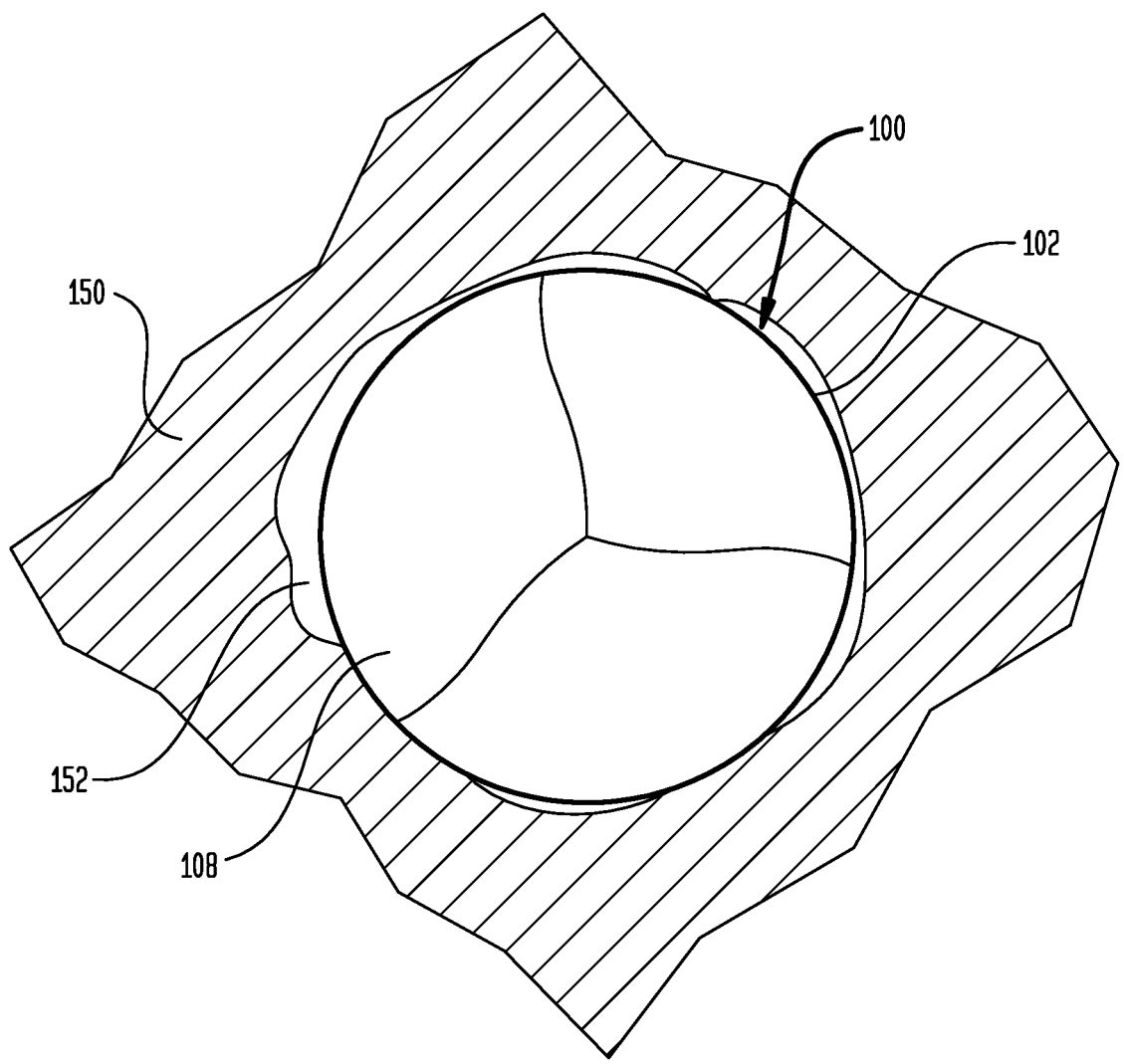
FIG. 2 is a top cross-sectional view of the prosthetic heart valve of FIG. 1 implanted in a patient taken along Line 2-2 in FIG. 1.

FIG. 2 is a cross-sectional illustration of the prosthetic heart valve 100 having leaflets 108 disposed within the native valve annulus 150, taken along line 2-2 shown in FIG. 1. As seen in FIG. 2, the substantially circular annulus section of the stent 102 is disposed within a non-circular native valve annulus 150. At certain locations around the perimeter of the prosthetic heart valve 100, gaps 152 form between the heart valve 100 and the native valve annulus. Blood flowing through these gaps and around the valve assembly 140 of the prosthetic heart valve 100 can result in paravalvular leak or regurgitation and other inefficiencies which can reduce cardiac performance. Such improper fitment may be due to suboptimal native valve annulus geometry due, for example, to calcification of the native valve annulus or due to unresected native leaflets.

In accordance with the various embodiments of the present disclosure, stent assemblies for use in a prosthetic heart valve incorporating multiple design concepts of a cuff feature for eliminating paravalvular leakage will be described. As to be described hereinafter in greater detail, one or more members may be coupled to a portion of the stent's cuff and to additional stent features such as the runners 114 to position the cuff about the abluminal surface of the stent upon deployment from a delivery device to seal in and around any calcific nodules. Prosthetic heart valves having such a cuff pursuant to the embodiments of the present disclosure decrease delivery system volume and profile of the prosthetic heart valve. The cuff sealing material being coupled to the members is positioned out of the area of most volume providing a low profile prosthetic heart valve. When deployed, the members, such as formed from shape memory materials, relax from their tensioned state and position the cuff sealing material in the sealing region of the prosthetic heart valve to reduce paravalvular leakage. Various embodiments of a prosthetic heart valve including a stent assembly having such a cuff pursuant to the present disclosure will now be described.

Figure 3:
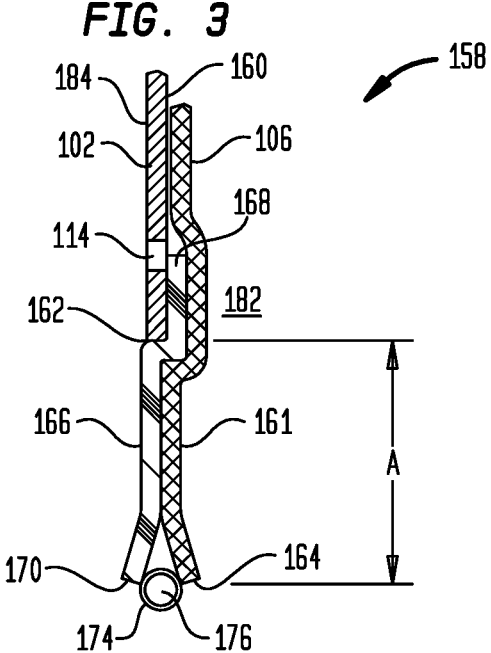
FIG. 3 is a cross sectional view of a prosthetic heart valve including a stent assembly having a cuff in accordance with one embodiment of the disclosure shown coupled to members in a tensioned state.
Figure 4:
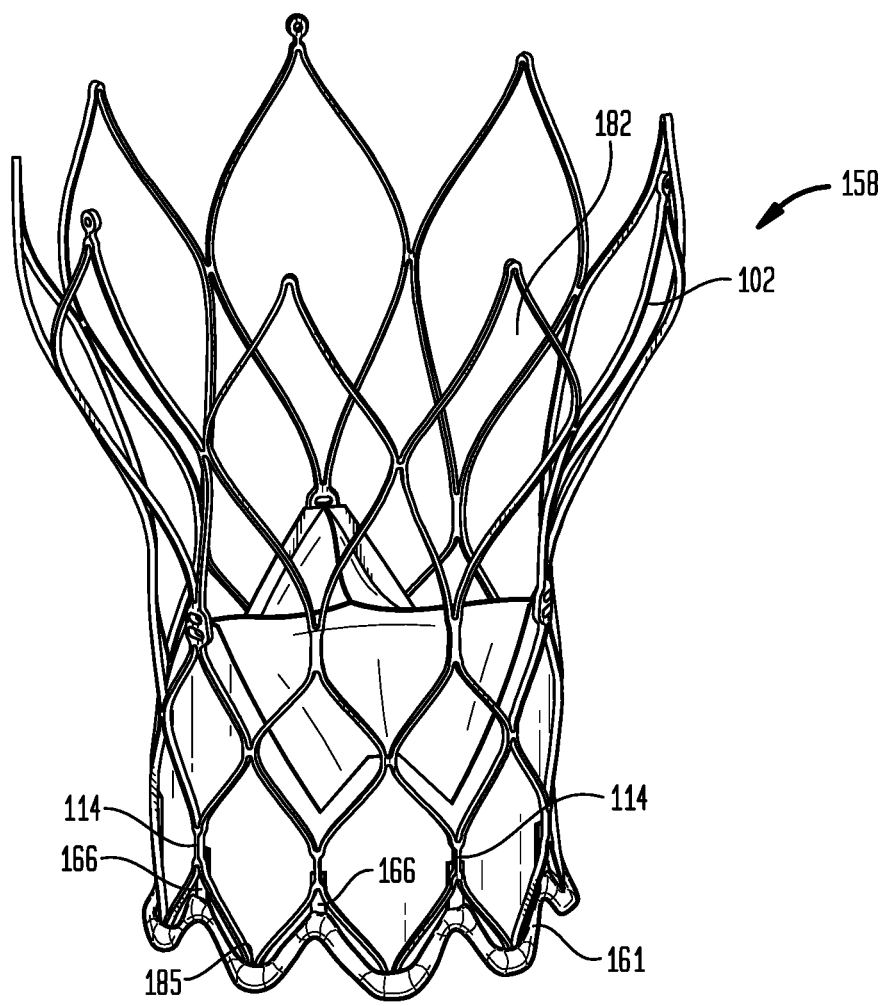
FIG. 4 is a perspective view of the prosthetic heart valve of FIG. 3 showing the members in a relaxed state forming a cuff seal.

Referring to FIGS. 3 and 4, a prosthetic heart valve 158 is shown which includes a stent 102 provided with a cuff 106 at least partially disposed over its luminal surface 160 such as shown in FIG. 1 thereby forming a stent assembly. The cuff 106 has an extended cuff portion 161 which extends outwardly beyond the proximal end 162 of the stent coupled to at least one member 166 shown under tension. In the embodiment being described, the distance between the proximal end 162 of the stent 102 and the proximal end 164 of the extended cuff portion 161 may be in one example about 2 mm as designated by dimension A. As will be understood from the various embodiments of the disclosure to be described, dimension A can be varied depending upon the desired position of the extended cuff portion 161 when positioned by the members 166. The cuff 106 and extended cuff portion 161 may be one integral unitary member, or two or more members sutured together. In either case, they may be formed from a variety of materials as previously described with respect to cuff 106, including, but not limited to bovine/porcine tissue (glycerol impregnated or freeze dried), radiopaque fabric/tissue, braided or woven fabric (PTFE, PET, UHMWPE), PTFE or gel/collagen coated fabric, multi-layered composite/sheets of any of these materials (e.g., fabric/tissue composites), etc.

The extended cuff portion 161 may be coupled to the stent 102 by a plurality of circumferentially arranged elongated members 166 positioned around the stent, and in particular, between the cuff and the stent to reduce stent volume or bulk. The distal end 168 of the members 166 may be attached to the runners 114 of the stent 102 between the cuff 106 and the stent frame using known suturing techniques. The proximal ends 170 of the members 166 and the proximal end 164 of the extended cuff portion 161 may be coupled to a ring shaped hollow tube 174 which defines a lumen 176. The hollow tube 174 can be constructed as a fabric tube from the same or different materials as the cuff 106 described above. The members 166 may be sutured to the hollow tube 174 using known suturing techniques, by way of example, using a single knotted stitch, followed by a double knot as known in the surgical field. On the other hand, the extended cuff portion 161 may be coupled to the hollow tube 174 using a running whip stitch as known in the surgical field.

The members 166, in accordance with the present disclosure, have dimensional and/or shape memory properties, which after being tensioned, will return to their original dimensions and/or shape after the tensioning force is removed, i.e., relaxed state. Suitable materials for the members 166 may comprise, by way of example, synthetic polymer material such as polypropylene and elastic silicones; natural rubber, super-elastic material, and elastic metals; and shape memory material and shape memory alloys such as Nitinol. The members 166 may be in accordance with one embodiment in the nature of an elongated rectangular strip such as an elastic band wherein the members may be placed under tension by elongating from their relaxed or original state. In other embodiments, the members 166 may be configured as elements which return to their original dimension and/or shape after a tension force is removed such as springs, e.g., coiled springs and the like. Upon release of the tension, the members will revert to their original length dimension and/or shape. In the embodiment described thus far with respect to FIGS. 3 and 4, the members 166 may be in the nature of bands of elastic material about 3 mm in width and about 4 mm in length when relaxed. In accordance with other embodiments, the members 166 may be in the nature of coiled springs of biocompatible material or shape memory material such as Nitinol. Accordingly, the members may have different forms and different material properties and characteristics to allow tensioning and then return to their original dimensions and/or shape after the tension force is removed.

In the embodiment shown in FIGS. 3 and 4, the distal ends 168 of the members 166 are attached to the nine runners 114 provided circumferentially about the stent 102 adjacent the stent's proximal end using any suitable technique, such as suturing and the like. However, the members 166 may also be attached to the stent's joints, struts or any other valve or stent feature. As best shown in FIG. 4, the runners 114 are located between adjacent cells forming the first proximal row of the stent frame 102. In the event of a greater number of cells and runners, it is contemplated that there will be a corresponding increase in the number of members 166 used for coupling the extended cuff portion 161 to the stent, although not a requirement of the disclosure. It is therefore not required that a member 166 be attached to each of the runners 114 or other attachment features on the stent 102. In particular, the number of members 166 may be less than the number of runners or other such features to which the members could be attached. In addition, it is not required that the members 166 be attached symmetrically about the stent 102; rather, the members can be attached asymmetrically about the stent and at different distances between the distal and proximal ends of the stent.

The members 166 as shown in FIG. 3 have been tensioned thereby positioning a portion of the extended cuff portion 161 outwardly of the proximal end 162 of the stent 102. This initial configuration produces a low profile stent as the extended cuff portion 161 (which will form the cuff seal) and members 166 are generally positioned within the lumen 182 formed by the stent frame as opposed to being supported externally on the abluminal surface 184 of the stent. The extended cuff portion 161 and members 166 can be pulled-up, twisted-up, folded-up, rotated-up, inverted-up and the like into the lumen 182 prior to positioning the stent 102 in the catheter of the delivery device. When being deployed from the delivery device, the members 166 will transform the shape of the extended cuff portion 161 from one of its aforementioned shapes into the final shape of the cuff seal as shown in the various embodiments of the disclosure. By way of one example, by pulling on and inverting the extended cuff portion from its delivery configuration or shape to its deployed configuration or shape thereby forming the cuff seal.

In the orientation disclosed in FIG. 3, the low profile stent 102 can be inserted, typically after being collapsed, into the lumen of a catheter delivery device for delivery to a native aortic valve using known surgical procedures and delivery devices. Upon removal from the delivery device, the members 166 will relax to their original non-tensioned state. As a result, the members 166 will pull the extended cuff portion 161 and the hollow tube 174 out of the lumen 182 and then over the stent's proximal edge towards the distal end of the stent. At least a portion of the extended cuff portion 161 and hollow tube 174 will now be disposed over the lower abluminal surface 184 of the stent adjacent the stent's proximal edge. By attaching the members 166 to the runners 114 adjacent the proximal end of the stent 102, the extended cuff portion 161 and hollow tube 174 are pulled upwardly over the proximal edge of the stent into an undulating cuff seal 185. The undulating pattern is provided by the bottom row of cells 112 forming the stent 102 which are open facing proximally as shown in FIG. 1. Accordingly, the extended cuff portion 161 and hollow tube 174 conform to the shape of the bottom most rows of cells 112 in the stent 102. The extended cuff portion 161 extends outwardly of the abluminal surface 184 of the stent for engagement with patient's tissue to form a seal thereat, thereby preventing paravalvular leakage.

Figure 5:
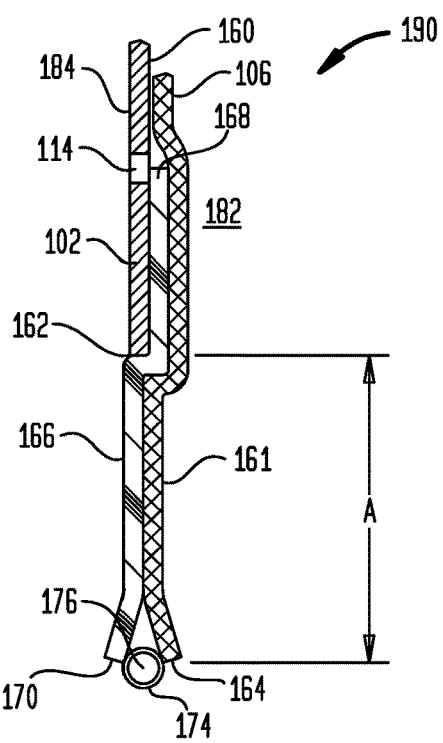
FIG. 5 is a cross sectional view of a prosthetic heart valve including a stent assembly having a cuff in accordance with another embodiment of the disclosure coupled to members in a tensioned state.
Figure 6:
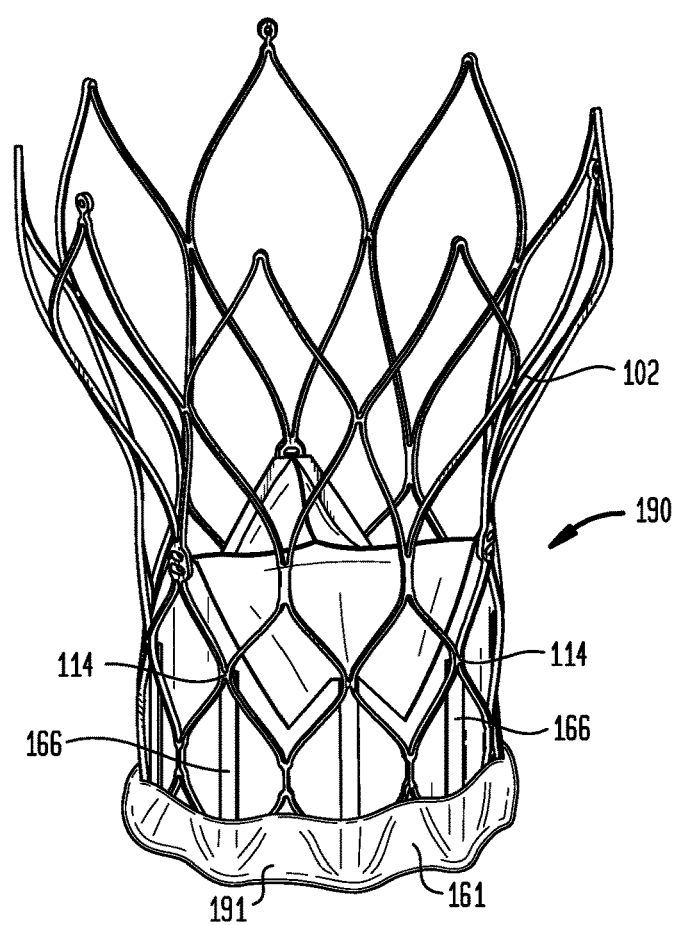
FIG. 6 is a perspective view of the prosthetic heart valve of FIG. 5 showing the members in a relaxed state forming a cuff seal.

Referring to FIGS. 5 and 6, another embodiment of a prosthetic heart valve 190 including a stent 102 having a cuff forming a stent assembly is disclosed. The prosthetic heart valve 190 is of similar construction to the prosthetic heart valve 158 disclosed in FIG. 3. In the prosthetic heart valve 190 of FIG. 5, the distal ends 168 of the members 166 are attached to the runners 114 at the mid-peak or mid-joint of the stent 102. In addition, the extended cuff portion 161 extends a greater distance beyond the proximal end 162 of the stent 102 than in the prosthetic heart valve 158 of FIG. 3. In accordance with this embodiment, the dimension A may be approximately 6 mm, i.e., the distance between the proximal end 162 of the stent 102 and the proximal end 164 of the extended cuff portion 161. It is contemplated that the members 166 will therefore be larger than those described in FIG. 3, for example, about 5 mm wide and about 8 mm long.

In FIG. 5, the members 166 are shown under tension by being elongated, thereby displacing the proximal end 164 of the extended cuff portion 161 outwardly from the proximal end 162 of the stent 102. The members 166 and extended cuff portion 161 are now configured to be generally confined within the lumen 182 of the stent upon insertion into a catheter of a delivery device. At the location of delivery of the prosthetic heart valve 190, the members 166 relax, thereby pulling the extended cuff portion 161 and hollow tube 174 out of the lumen 182 and then in a direction towards the distal end of the stent. As a result, a portion of the extended cuff portion 161 is arranged overlying and circumscribing the abluminal surface 184 of the stent as shown in FIG. 6. As the members 166 are attached to runners 114 at the mid-peak or mid-joint of the stent, i.e., distally displaced further away from the runners as shown in the embodiment of FIG. 3, the extended cuff portion 161 and hollow tube 174 form a gathered ring of cuff sealing material 191 circumscribing adjacent the proximal end 162 of the stent 102, generally lacking the previous undulating pattern.

Figure 7A:
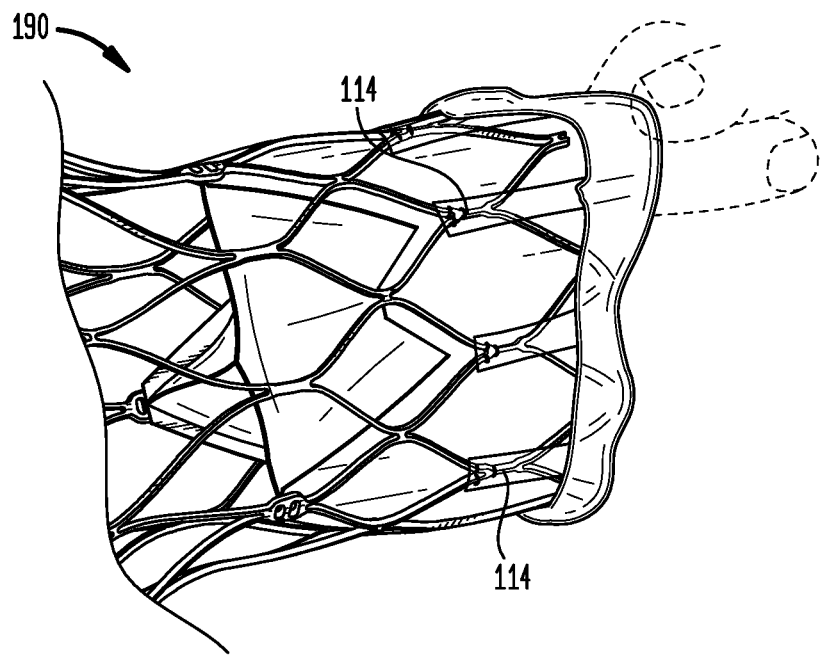
FIGS. 7A and 7B are perspective views of the prosthetic heart valve of FIG. 6 being prepared for insertion into the lumen of a catheter delivery system by placing the members under tension.
Figure 7B:
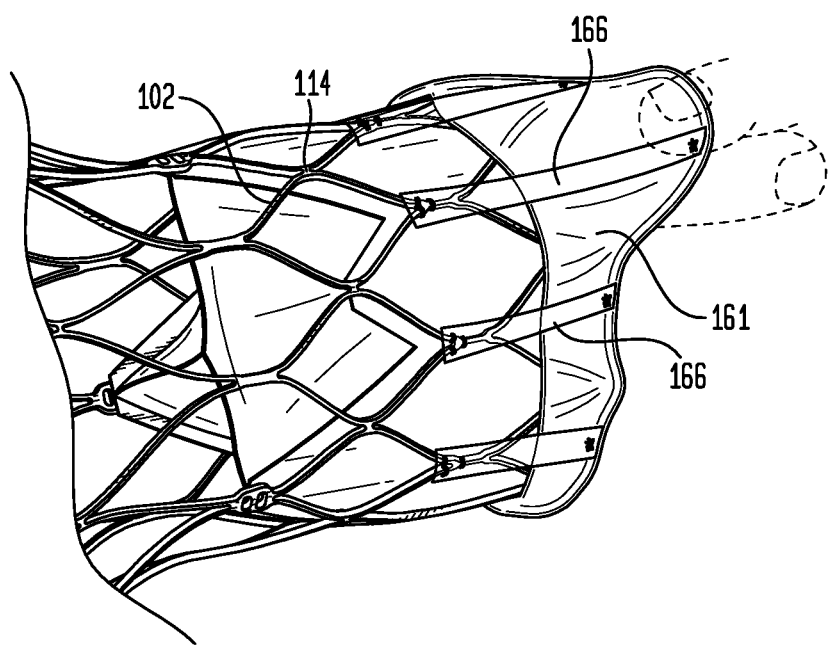
Figure 8:
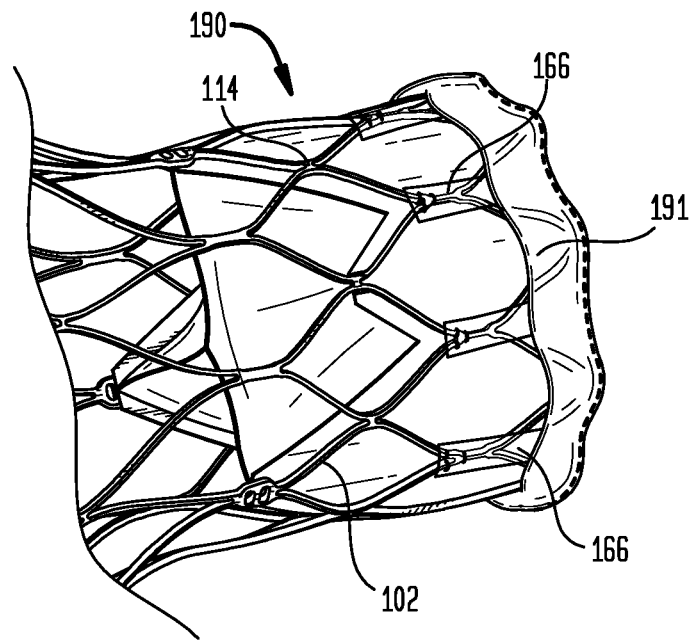
FIG. 8 is a perspective view of the prosthetic heart valve shown in FIG. 7 after being deployed from the delivery system.

Referring to FIGS. 7A and 7B, the prosthetic heart valve 190 is shown being prepared to be received within a catheter of a delivery device. The extended cuff portion 161 is pulled against the resistance of the members 166 from their relaxed orientation (FIG. 7A) in an outwardly proximal direction around the stent to place the members 166 under tension, as shown in FIG. 7B. The extended cuff portion 161 is then finally positioned within the lumen 182 to reduce bulk volume during sheathing of the stent. In FIG. 8, the prosthetic heart valve 190 is shown after deployment from the delivery device where the members 166 have relaxed with the extended cuff portion 161 and hollow tube 174 arranged circumscribing the proximal end of the stent 102 overlying the abluminal surface 184 forming the cuff seal 191.

Figure 9:
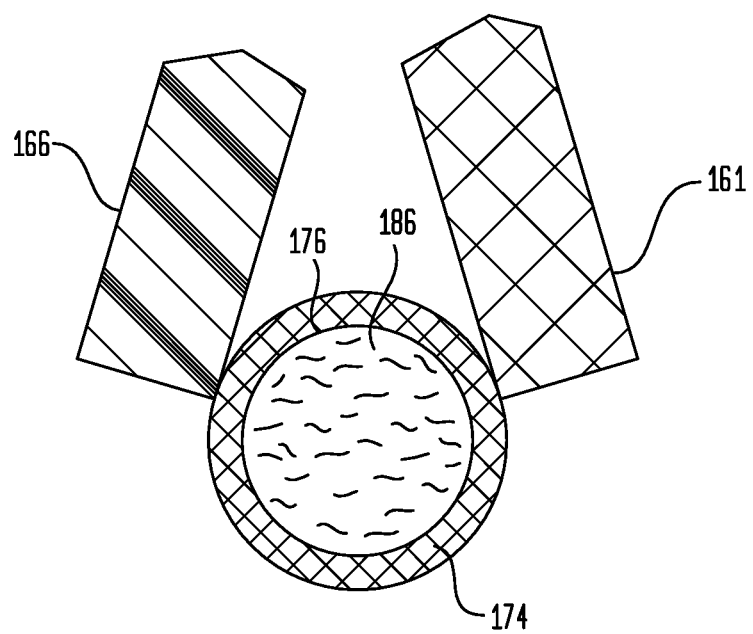
FIG. 9 is a cross sectional view of the fiber hollow tube of the prosthetic heart valve of FIGS. 3 and 5 including an insert in the nature of filler material.

To enhance the sealing effect of the cuff to prevent paravalvular leakage, the hollow tube 174 may contain an insert such as filler material or an elongated coiled member. By way of example, as shown in FIG. 9, the lumen 176 of the hollow tube 174 has been filled with expandable material 186. By way of example, expandable material 186 may include PVA, polyacrilimide, shape memory foam, collagen, and the like to increase sealing bulk. Further, the filler material 186 may include a highly compressible sponge made from alginate cross linked at low temperature. This type of gel will collapse to a large extent when shear forces are applied and return to its original shape when the forces are removed. As a result of the compressibility of this type of material, it will contribute to a low prosthetic heart valve profile, and will spring back when deployed to provide an effective paravalvular leak seal. It is further contemplated that other biocompatible materials can be used for the filler material 186 in accordance with other embodiments of the present disclosure.

Figure 10:
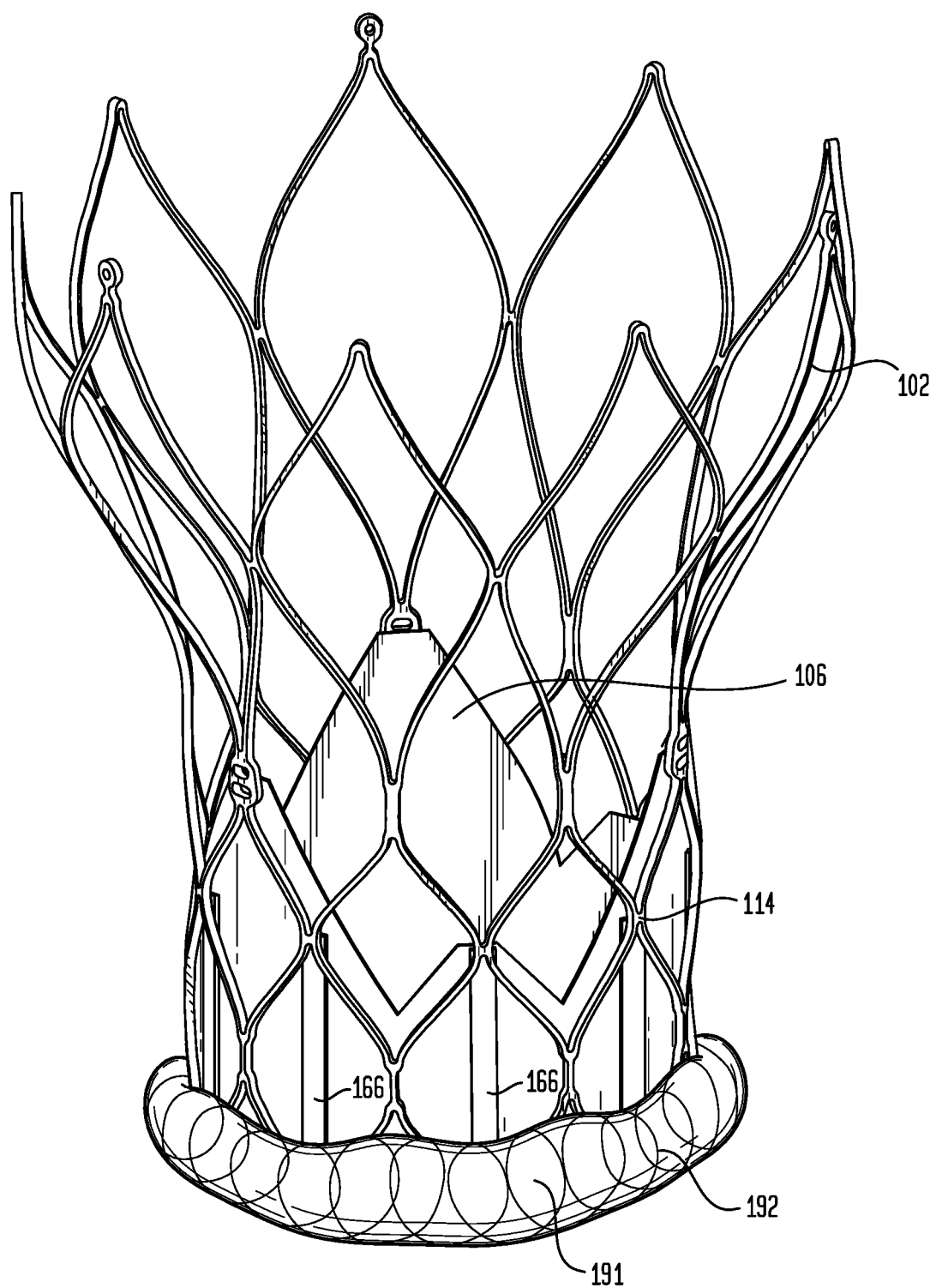
FIG. 10 is a perspective view of the prosthetic heart valve showing the fiber hollow tube of FIGS. 3 and 5 having an insert in the nature of a coiled member.

As shown in FIG. 10, the insert may include an elongated coil member 192 or other shaped members formed from various materials such as biocompatible polymers and metals and metal alloys. For example, the coil member 192 may be formed of materials similarly used for the construction of the stent 102 such as Nitinol which can be collapsed and then returned to its original shape after deployment of the stent.

Figure 11:
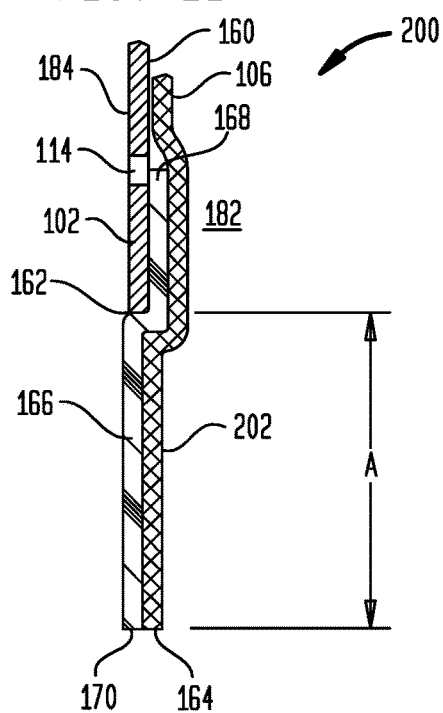
FIG. 11 is a cross sectional view of a prosthetic heart valve including a stent assembly having a cuff in accordance with another embodiment of the disclosure coupled to members in a tensioned state.
Figure 12:
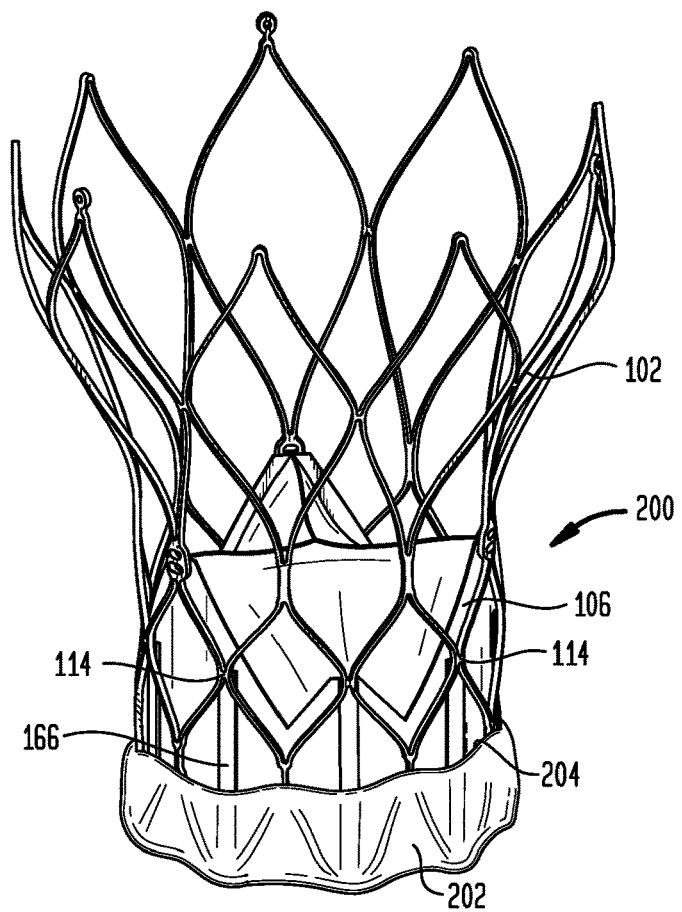
FIG. 12 is a perspective view of the prosthetic heart valve of FIG. 11 showing the members in a relaxed state forming a cuff seal.

Referring now to FIGS. 11 and 12, another embodiment of a prosthetic heart valve 200 having a stent assembly will be described. As shown in FIG. 11, as in the previous embodiments, the prosthetic heart valve 200 includes a cuff 106 coupled to the stent 102 disposed over the luminal surface 160 and a plurality of members 166 shown under tension thereby forming a stent assembly. The distal ends 168 of the members 166 are coupled between the cuff 106 and stent 102 to the runners 114 at the stent's mid-joint or mid-peak, circumferentially around the stent using known suturing techniques. The cuff 106 is provided with an extended cuff portion 202 projecting outwardly from the proximal end 162 of the stent 102. By way of one example, the extended cuff portion 202 may have a length of approximately 9 mm below the proximal end 162 of the stent. In this embodiment, the members 166 formed of elastic material may have a width of about 5 mm and a length of about 8 mm. The proximal ends 170 of the members 166 are sutured to the proximal end 164 of the extended cuff portion 202 by suitable suturing techniques, such as using a single/double knot on the abluminal side as is known in the surgical field.

As shown in FIG. 12, when the members 166 are relaxed from their tensioned state as shown in FIG. 11, the members recoil and pull the extended cuff portion 202 out of the lumen 182 and then in a direction towards the distal end of the stent 102 over a portion of the abluminal surface 184 of the stent. This forms a continuous expandable pocket 204 between the extended cuff portion 202 and abluminal surface 184 of the stent 102 about the annulus section 104. The pocket 204 is open facing in a distal direction circumscribing the stent 102, while closed facing in a proximal direction. The height of the pocket can be modified by changing the length of the extended cuff portion 202. The pocket 204 receives fluid pressure in the patient's artery when deployed as an aortic valve to expand and seal around calcified nodules.

Figure 13:
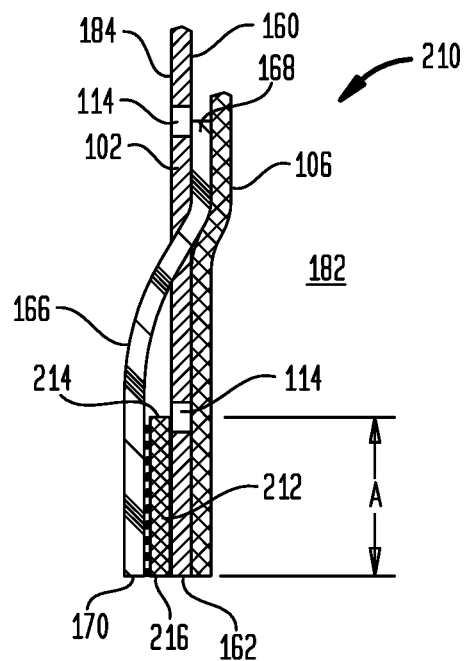
FIG. 13 is a cross sectional view of a prosthetic heart valve including a stent assembly having a cuff in accordance with another embodiment of the disclosure coupled to members in a tensioned state.
Figure 14:
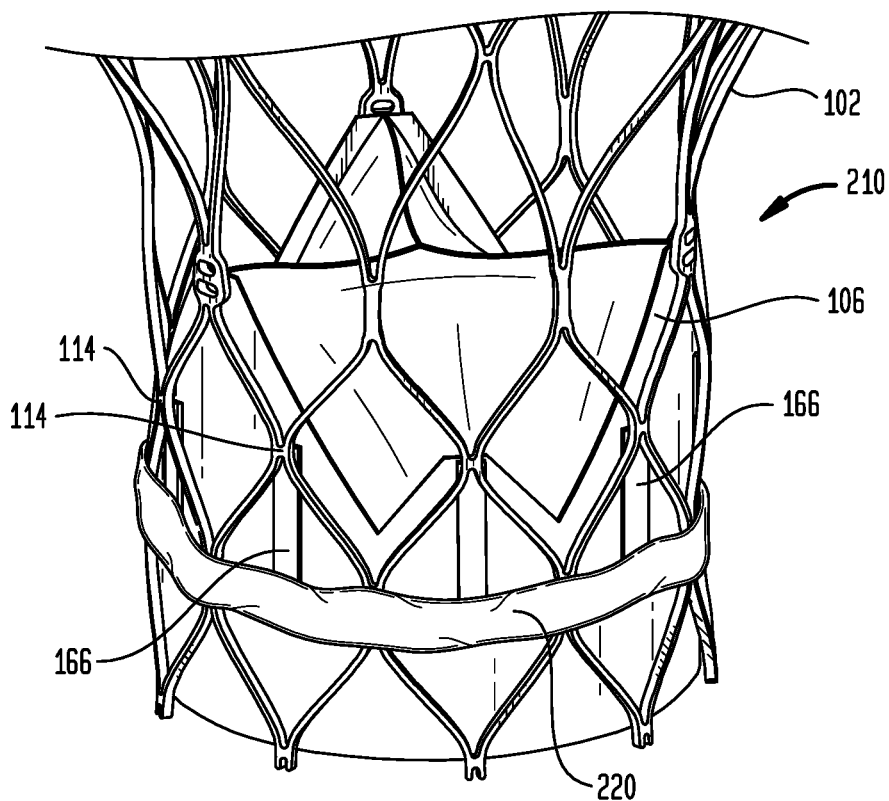
FIG. 14 is a perspective view of the prosthetic heart valve of FIG. 13 showing the members in a relaxed state forming a cuff seal.

Referring now to FIGS. 13-14, there will be described a prosthetic heart valve 210 having a stent assembly in accordance with another embodiment of the present disclosure. As shown in FIG. 13, the members 166 under tension have their distal ends 168 coupled to the runners 114 at the mid-joint or mid-peak of the stent 102 between the cuff 106 and the stent using suitable suturing techniques, thereby reducing the bulk or volume of the stent. The members 166 extend outwardly overlying the abluminal surface 184 of the stent 102 in a proximal direction. The proximal ends 170 of the members 166 are generally arranged adjacent the proximal end 162 of the stent 102.

As previously described, the members 166 may be constructed in the nature of elongated bands of elastic material. In the embodiment of FIG. 13, the members 166 may be approximately 5 mm in width and 8 mm in length. A panel 212 of sealing material is arranged overlying the abluminal surface 184 of the stent 102 adjacent the proximal end 162 of the stent. The sealing material 212 may be in the nature of a rectangular elongated panel circumscribing the stent 102. The sealing material 212 can be provided from material similar to cuff 106 so as to form a seal to prevent paravalvular leakage when the prosthetic heart valve 210 is positioned in a native aortic valve. In this embodiment the panel 212 may have a height of about 9 mm.

The distal end 214 of the panel of sealing material 212 is coupled to runners 114 about the circumference of the stent 102 using any suitable suturing technique as known in the art. The proximal end 216 of the panel of sealing material 212 terminates adjacent the proximal end 162 of the stent 102 and is not attached thereto. Rather, the proximal ends 170 of the members 166 are coupled on the abluminal side to the proximal end 216 of the panel of sealing material 212 using a single/double knot as is known in the surgical field. In addition, each of the members 166 is coupled to the panel of sealing material 212 using an alternating running stitch from the distal end 214 to the proximal end 216 of the sealing material along longitudinal axes of the stent 102 while the members are under tension by being elongated.

Referring to FIG. 14, when the members 166 are relaxed, the relaxed state causes the panel of sealing material 212 to fold back upon itself in a direction towards the distal end of the stent over the abluminal surface 184 of the stent 102 to create a bunched-up ring of sealing material 220 at the location of the runner 114 to which the distal end 214 of the sealing material was attached. The location of the sealing material can be changed by altering the runner attachment location along the stent in the proximal/distal direction.

Although certain embodiments of the prosthetic heart valve having a stent assembly as described herein may provide a single feature for reducing paravalvular leakage, it should be understood that multiple similar or dissimilar features may be utilized on a single prosthetic heart valve to reduce paravalvular leakage. Various embodiments of a low profile prosthetic heart valve have been described in accordance with the present disclosure. In certain embodiments, an extended cuff is coupled to the stent with a plurality of members in the nature of elongated shape memory material such as elastic members or shape memory members, or coiled members to provide a low profile prosthetic heart valve for catheter delivery. The members are initially placed under tension to maintain an extended cuff portion in a first orientation such as outwardly of the proximal end of the stent. Upon relaxing the tension in the members, the extended cuff portion is pulled towards the distal end of the stent over the abluminal surface to form a cuff seal at various locations along the stent in the annulus section. In some embodiments, the cuff seal is in the nature of a circumscribing expandable pocket, the height of which can be modified. Prosthetic heart valves with expandable pockets are described in greater detail in U.S. Patent Publication No. 2011/0098802, the disclosure of which is hereby incorporated by reference herein. In other embodiments of the present disclosure, a panel of sealing material may be placed circumferentially about the abluminal surface of the stent to which the members are coupled. In the various embodiments, the members remain coupled to the cuff material and stent as an integral component of the prosthetic heart valve when replacing native valves.

A prosthetic heart valve incorporating a stent assembly for replacing a native valve in accordance with one embodiment of the disclosure is constructed from a stent having a luminal surface and an abluminal surface extending between a distal end and a proximal end thereof; a valve may be disposed within the stent; a cuff coupled to the stent having a first orientation and a second orientation; and a plurality of members having a distal end coupled to the stent and a proximal end coupled to the cuff, the plurality of members having a first state when the cuff is arranged in the first orientation and a second state when the cuff is arranged in the second orientation.

In the aforesaid prosthetic heart valve, wherein the plurality of members have a distal end and a proximal end, and wherein the proximal ends of the plurality of members are coupled to the cuff at spaced apart circumferential locations around the stent; and/or wherein the stent includes a plurality of runners, and wherein the distal ends of the plurality of members are coupled to the runners; and/or wherein the cuff includes a distal end and a proximal end, and wherein the plurality of members include a distal end and a proximal end, and further including a hollow tube coupled to the proximal ends of the cuff and the plurality of members; and/or wherein the hollow tube defines a lumen, and further including an insert disposed within the lumen; and/or wherein the insert comprises at least one of a filler material or an elongated coiled member; and/or wherein the plurality of members are attached to the cuff circumferentially along spaced apart longitudinally extending axes of the stent; and/or wherein at least a portion of the cuff is at least partially positioned outward of the proximal end of the stent when arranged in the first orientation and at least partially disposed on the abluminal surface of the stent when arranged in the second orientation; and/or wherein the members comprise elastic members having a tensioned first state and a relaxed second state.

A prosthetic heart valve incorporating a stent assembly for replacing a native valve in accordance with one embodiment of the disclosure is constructed from a stent having a proximal end and an abluminal surface; a valve may be disposed within the stent; and a cuff coupled to the stent by a plurality of members having a relaxed state and a tensioned state for orienting at least a portion of the cuff at least partially disposed on the abluminal surface when the plurality of members are in a relaxed state.

In the aforesaid prosthetic heart valve, wherein at least a portion of the cuff is arranged at least partially outward of the proximal end of the stent when the plurality of members are in a tensioned state; and/or wherein the stent includes a plurality of runners, and wherein the plurality of members have a distal end and a proximal end, the distal end of the plurality of members is coupled to one of the runners and the proximal end of the plurality of members is coupled to a portion of the cuff; and/or wherein the cuff is at least partially disposed on the abluminal surface of the stent when the plurality of members are in the tensioned state and relaxed state; and/or wherein the plurality of members are attached to the cuff circumferentially along spaced apart longitudinally extending axes of the stent; and/or wherein the cuff includes a distal end and a proximal end, and wherein the plurality of members include a distal end and a proximal end, and further including a hollow tube coupled to the proximal ends of the cuff and the plurality of members, and an insert comprising at least one of a filler material or an elongated coiled member disposed within the hollow tube; and/or wherein the plurality of members comprise elastic members.

A prosthetic heart valve incorporating a stent assembly for replacing a native valve in accordance with one embodiment of the disclosure is constructed from a stent configured to have a collapsed condition and an expanded condition, the stent having a luminal surface and an abluminal surface extending between a distal end and a proximal end thereof; and a valve assembly may be disposed within the stent, the valve assembly including a plurality of leaflets and a cuff having a portion at least partially disposed on the luminal surface of the stent; at least a portion of the cuff having a first orientation extending outwardly of the proximal end of the stent or at least partially disposed on the abluminal surface of the stent, and a second orientation with a portion of the cuff at least partially disposed on the abluminal surface of the stent; and a plurality of elongated elastic members having a distal end coupled to the stent and a proximal end coupled to the cuff at circumferentially spaced apart locations, the plurality of elastic members having a tensioned state when the cuff is arranged in the first orientation and a relaxed state when the cuff is arranged in the second orientation.

In the aforesaid prosthetic heart valve, wherein the stent includes a plurality of runners, and wherein the distal ends of the plurality of elastic members are coupled to the runners; and/or wherein the cuff includes a distal end and a proximal end, and wherein the plurality of elastic members include a distal end and a proximal end, and further including a hollow tube coupled to the proximal end of the cuff and the plurality of elastic members, and an insert comprising at least one of a filler material or an elongated coiled member disposed within the hollow tube; and/or wherein at least a portion of the cuff is at least partially disposed on the abluminal surface of the stent when arranged in the second orientation and at least partially positioned outward of the proximal end of the stent when arranged in the first orientation; and/or wherein the cuff is at least partially disposed on the abluminal surface of the stent when the plurality of elastic members are in the first orientation and second orientation.

A stent assembly for use in replacing a native heart valve in accordance with one embodiment of the disclosure is constructed from a stent; a cuff coupled to the stent having a first orientation and a second orientation; and a plurality of members coupled between the stent and cuff, the members configured to arrange the cuff between the first and second orientations, wherein the members remain coupled to the stent and cuff after replacement of the native valve.

In the aforesaid prosthetic heart valve, wherein the stent defines a lumen, and wherein the cuff when arranged in the first orientation is disposed within the lumen, and wherein the cuff when arranged in the second orientation is disposed circumscribing the stent overlying an abluminal surface thereof forming a cuff seal; and/or wherein the inverting members comprise at least one of an elastic member and a coiled member having a tensioned first state and a relaxed second state; and/or wherein the inverting members are in a tensioned state when the cuff is in the first orientation and a relaxed state when the cuff is in the second orientation.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure.

The invention claimed is:

1. A prosthetic heart valve, comprising:
a stent having a proximal end, a distal end, a luminal surface defining a lumen through the stent and an abluminal surface opposite the luminal surface, the stent having an expanded condition and a collapsed condition;
a first cuff positioned on the luminal surface of the stent and a second cuff having a deployed configuration in which a region of the second cuff is spaced from the abluminal surface of the stent and an initial configuration in which the region of the second cuff is positioned against the abluminal surface of the stent, the deployed configuration being inverted relative to the initial configuration; and
a valve assembly disposed in the lumen of the stent.

2. The prosthetic heart valve as claimed in claim 1, wherein the second cuff is formed of a polymer.

3. The prosthetic heart valve as claimed in claim 1, wherein the second cuff is formed of a fabric.

4. The prosthetic heart valve as claimed in claim 1, wherein the first cuff is formed of plural layers of material.

5. The prosthetic heart valve as claimed in claim 1, wherein the second cuff is formed of multiple layers of material.

6. The prosthetic heart valve as claimed in claim 5, wherein the multiple layers of material include multiple polymer layers.

7. The prosthetic heart valve as claimed in claim 1, wherein the second cuff in the deployed configuration is spaced from the proximal end of the stent.

8. The prosthetic heart valve as claimed in claim 1, wherein the second cuff in the deployed configuration forms a bunched-up ring of material around an exterior of the stent.

9. The prosthetic heart valve as claimed in claim 1, wherein the second cuff moves from the initial configuration to the deployed configuration upon movement of the stent from the collapsed condition to the expanded condition.

10. The prosthetic heart valve as claimed in claim 5, wherein the multiple layers of material include multiple fabric layers.

11. A prosthetic heart valve, comprising:
a stent having a proximal end, a distal end, a luminal surface defining a lumen through the stent and an abluminal surface opposite the luminal surface, the stent having an expanded condition and a collapsed condition;
a first cuff positioned on the luminal surface of the stent and a second cuff having a first edge extending in a circumferential direction and a second edge extending in the circumferential direction, the second cuff having a deployed configuration in which both the first edge and the second edge are spaced from the proximal end of the stent and a region of the second cuff is spaced from the abluminal surface of the stent and an initial configuration in which the first edge is positioned adjacent the proximal end of the stent and the region of the second cuff is positioned against the abluminal surface of the stent; and
a valve assembly disposed in the lumen of the stent.

* * * * *